United States Patent [19]
Yamada et al.

[11] Patent Number: 5,885,978
[45] Date of Patent: Mar. 23, 1999

[54] EXTERNAL THERAPEUTIC COMPOSITION FOR DERMATITIS

[75] Inventors: Hajime Yamada; Akira Yamada, both of Nagareyama, Japan

[73] Assignee: CAC Corporation, Nagareyama, Japan

[21] Appl. No.: 626,963

[22] Filed: Apr. 3, 1996

[30] Foreign Application Priority Data

Dec. 11, 1995 [JP] Japan ................... 7-346006

[51] Int. Cl.$^6$ .................................. A61K 31/56
[52] U.S. Cl. .................... 514/177; 514/169; 514/170; 514/178; 514/179; 514/180; 514/181; 514/182
[58] Field of Search ................... 514/169, 170, 514/177, 178, 179, 180, 181, 182

[56] References Cited

U.S. PATENT DOCUMENTS

| | | | |
|---|---|---|---|
| 4,383,992 | 5/1983 | Lipari | 514/174 |
| 4,596,795 | 6/1986 | Pitha | 514/58 |
| 4,877,774 | 10/1989 | Pitha et al. | 514/26 |
| 5,019,562 | 5/1991 | Folkman et al. | 514/58 |
| 5,126,135 | 6/1992 | Yamada et al. | 424/401 |
| 5,229,370 | 7/1993 | Ammeraal | 514/26 |
| 5,505,847 | 4/1996 | Yamada et al. | 210/169 |

FOREIGN PATENT DOCUMENTS

| | | |
|---|---|---|
| 0 326 196 A2 | 8/1989 | European Pat. Off. . |
| 0 463 653 A1 | 1/1992 | European Pat. Off. . |
| 0 579 435 A1 | 1/1994 | European Pat. Off. . |
| 2 12443 | 3/1990 | Japan . |
| 3 240730 | 10/1991 | Japan . |
| 5 317859 | 12/1993 | Japan . |
| 7 8014 | 3/1995 | Japan . |
| 7 56417 | 6/1995 | Japan . |
| 8 10302 | 1/1996 | Japan . |
| 1 480 518 | 7/1977 | United Kingdom . |

OTHER PUBLICATIONS

K. Uekama et al., "Inclusion Complexations of Steroid Hormones with Cyclodextrins in Water and in Solid Phase", Chemical Abstracts, vol. 96, No. 18, p. 411, Abstract No. 149046j, May 3, 1982.

Husa "Pharmaceutical dispensing" Husa Brothers Pub. p. 228, 1947.

Okada et al. "Some properties and the inclusionbehavio of branched cyclodextrins" chem. Pharm. Bull. v. 36, pp. 2176–2185, 1988.

*Primary Examiner*—Ceila Chang
*Attorney, Agent, or Firm*—Oblon, Spivak, McClelland, Maier & Neustadt, P.C.

[57] ABSTRACT

The present invention provides an external therapeutic composition for dermatitis comprising an aqueous solution including a therapeutically effective amount of an adrenal cortical steroid, a cyclodextrin, polysaccharides, and a carrier such as water, prepared by clathrating the adrenal cortical steroid in the cyclodextrin using a homomixer to form a clathrate, and adding the clathrate to an aqueous solution of polysaccharides, while being stirred uniformly, to dissolve the clathrate in the aqueous solution, as well as a method for the treatment of dermatitis in a mammalian subject, which comprises administering to said subject a therapeupically effective amount of the external therapeutic composition for dermatitis described above. The external therapeutic composition for dermatitis according to the present invention is extremely safe and can cure dermatitis such as an atopic dermatitis or the like without side effects.

10 Claims, No Drawings

EXTERNAL THERAPEUTIC COMPOSITION FOR DERMATITIS

FIELD OF THE INVENTION

The present invention relates to an external therapeutic composition for dermatitis which can produce excellent therapeutic effects with respect to atopic dermatitis, seborrhea dermatitis, eczema, and the like, as well as being extremely safe.

RELATED ART

Heretofore, a steroid agent including an adrenal cortical steroid with a strong anti-inflammatory action has been mainly employed in the treatment of dermatitis such as atopic dermatitis and the like. The steroid agent of this type is generally in the form of a cream, with vaseline, methyl cellulose, surfactants, synthetic resin emulsions, powders, and the like, depending on the purpose. In some cases, it may be in the form of a liquid including surfactants.

In addition, there is another external composition which is safe and has purposes of (1) a pasteurizing or disinfecting action on the skin, (2) a membrane action, (3) an action to promote the moisturizing by preventing the moisture on the skin from evaporating, and the like. In the external composition of this type, inorganic salts such as sodium chloride and the like (U.S. Pat. No. 3,574,854), natural sugars such as glucose and the like (U.S. Pat. No. 3,859,436), or plasma (U.S. Pat. No. 3,777,597) are employed as a combination agent.

In addition, the present inventors previously proposed an aqueous cosmetic composition for the skin and/or hair which is safe as well as produces the same conditions as the cutaneous cellular interstitial fluid on the skin surface, maintains the normal electrolyte balance and osmotic pressure balance, and promotes the normalization of diseased cells from the cutaneous surface, by virtue of containing glucose and sodium chloride in polysaccharides, in order to activate the cutaneous cells and improve the diseases caused by the lowering of the cell functions of the cutaneous cells (Japanese Patent No. 1,597,430).

An adrenal cortical steroid exhibits superior pharmaceutical effects such as depression of fibroblast growth, an anti-inflammatory action, and the like, while it exhibits poor effects in the treatment of the atopic dermatitis or the like. Although the reasons the effects of the adrenal cortical steroid vary are not clear, it is hypothesized that the oily ingredients for formulating an ointment or a cream dissolve the cutaneous horny layer and block the regeneration of the normal skin. In addition, the inhibition of pituitary—adrenal cortex functions as well as the side effects such as functional disorders in eyes and the other organs caused by the use of a large amount of the adrenal cortical steroid may be observed. In order to avoid the disadvantages described above, it is desired that the dose amount of steroids be reduced, while the pharmaceutical effects as an anti-inflammatory agent be maintained.

Another external composition, which is safe, employing sodium chloride and the like is not admitted from the point of view of the effects in the treatment of dermatitis such as atopic dermatitis, even if the composition can enhance the skin pasteurization and protection such as moderating the skin, making the skin healthful, smoothing the skin, and the like.

On the other hand, in an aqueous solution of a cosmetic composition for the treatment of the skin and hair which the present inventors previously proposed, it has been proved that the cosmetic aqueous solution activates the cells of the skin, the tunica mucosa nasi, and the like, as well as exhibits superior effects against the diseases such as alopecia, pigmentation, stomatitis, hay fever, and the like.

There are various factors which contribute to the development of various dermatitides such as eczema, allergic dermatitis, atopic dermatitis, and the like, but the critical cause has not yet been elucidated. However, when considering only the changes on the cellular level, the cause of the dermatitides lies in the disfunction of the cell membrane and the membranes of the mitochondria which are one of the intracellular organelles. In other words, in the inflamed skin, inhibition of intracellular respiration occurs because of a disorder in the mitochondrial membrane, reducing the production of ATP (adenosine triphosphate) which is an energy source of the cell. The active transport function of the cellular membrane is lowered owing to the lack of ATP, lowering in the ability to transport the substances between the cells and the interstitial fluid. It causes the lack of the nutritive substances such as glucose and the like within the cell, linking to the depression of the ATP production. For this reason, such a vicious circle may be formed.

Therefore, in consideration of the above conditions, the present inventors have directed their attention to use of an aqueous base containing polysaccharides, instead of oily ingredients (surfactants) which are commonly employed in a therapeutic external composition containing an adrenal cortical steroid, based on the suspicion that the oily ingredients for forming an ointment or a cream combined with the adrenal cortical steroid may cause the inhibition of intracellular respiration by the disfunction of the mitochondrial membrane.

SUMMARY OF THE INVENTION

It is an object of the present invention to provide a therapeutic external agent for dermatitis which is extremely safe, by virtue of forcing the adrenal cortical steroid (which is slightly soluble in water) to dissolve in an aqueous solution, wherein the dermatitis such as atopic dermatitis and the like can be completely cured without fear of side effects.

The object according to the present invention have been achieved by providing an external therapeutic composition for dermatitis comprising an aqueous solution including a therapeutically effective amount of an adrenal cortical steroid, a cyclodextrin, polysaccharides, and a carrier.

Another object according to the present invention have been achieved by providing a method for the treatment of dermatitis in a mammalian subject, which comprises administering to said subject a therapeupically effective amount of an external therapeutic composition for dermatitis comprising an aqueous solution including a therapeutically effective amount of an adrenal cortical steroid, a cyclodextrin, polysaccharides, and a carrier.

DISCLOSURE OF THE INVENTION

According to the present invention, the external therapeutic composition for dermatitis comprising an aqueous solution including a therapeutically effective amount of an adrenal cortical steroid, a cyclodextrin, polysaccharides, and a carrier which is water, is prepared by clathrating the adrenal cortical steroid in the cyclodextrin using a homomixer to form a clathrate, and adding the clathrate to an aqueous solution of polysaccharides, while being stirred uniformly, to dissolve the clathrate in the aqueous solution.

In the present invention, in order to dissolve the adrenal cortical steroid, which is only slightly soluble in water, in an aqueous solution, the adrenal cortical steroid is previously clathrated in the cyclodextrin.

As the adrenal cortical steroid, there can be mentioned diflorazones, hydrocortisones, methyl prednisolones, dexamethasones, betamethasones, and the like. The adrenal cortical steroid may be present in the amount of 0.025% by weight to 0.5% by weight based on the total weight of the external therapeutic composition according to the present invention. The cyclodextrine for clathrating the adrenal cortical steroid may be included in the amount of 0.2% by weight to 30% by weight based on the total weight of the external therapeutic composition according to the present invention.

As the polysaccharides contained in the aqueous solution for dissolving the adrenal cortical steroid, there can be mentioned dextran, pullulan, or the like. They may be present in the amount of 0.5% by weight to 55% by weight based on the total weight of the external therapeutic composition according to the present invention.

In addition, the aqueous solution for dissolving the adrenal cortical steroid may comprise glucose, mutan, lentinan, sodium chloride, calcium chloride, and potassium chloride, other than the polysaccharides.

By virtue of the aqueous solution of this type, the same circumstances as the cellular interstitial fluid may be provided on the cutaneous surface, promoting the normal activity of the cells. For this reason, a synergistic effect between the natural healing power which the living organism has per se and the adrenal cortical steroid agent can be obtained.

In the following, the therapeutic external agents for dermatitis according to the present invention will be explained in detail by reference to Formulation Examples and Pharmaceutical Test Examples.

FORMULATION EXAMPLE 1

| | |
|---|---|
| Dextran | 10 g |
| Glucose | 10 g |
| Maltose | 5 g |
| Mannitol | 15 g |
| Sodium chloride | 0.2 g |
| Betamethasone | 0.06 g |
| Cyclodextrin | 15 g |
| Purified water | 44.74 g |
| Total | 100.0 g |

The formulation according to Formulation Example 1 was prepared by preparing a 10% aqueous solution of cyclodextrin using a part of the purified water, adding betamethasone to the aqueous solution while being stirred, and adding the rest of the purified water, salts, and saccharides thereto.

In the following, the effects of Formulation Example 1 are shown.

TABLE 1

| Disease | Number of Subjects | Effectiveness (Points) | Effective Rate (%) |
|---|---|---|---|
| Atopic dermatitis (1) | 25 | 48 | 96 |
| Atopic dermatitis (2) | 10 | 19 | 95 |
| Atopic dermatitis (3) | 25 | 46 | 92 |

TABLE 1-continued

| Disease | Number of Subjects | Effectiveness (Points) | Effective Rate (%) |
|---|---|---|---|
| Atopic dermatitis (4) | 25 | 49 | 98 |
| Seborrhea dermatitis (1) | 25 | 48 | 96 |
| Seborrhea dermatitis (2) | 100 | 198 | 99 |
| Seborrhea dermatitis (3) | 10 | 19 | 95 |
| Psoriasis vulgaris | 5 | 9 | 90 |
| Eczema | 25 | 48 | 96 |
| Acne | 50 | 99 | 99 |

Table 1 shows the results of the pharmaceutical tests with regard to Formulation Example 1. In Table 1, "Effectiveness" is shown by the total points according to the evaluation as follows:

Evaluation:

0 point Unchanged after using Formulation Example 1

1 point Curing change is observed after using Formulation Example 1

2 points Curing effects are confirmed after using Formulation Example 1

"Effective rate" in Table 1 is calculated according to the following mathematical expression:

Effective Rate={(Total points)/(Number of subjects)×2}×100

The data with regard to atopic dermatitis in Table 1 are based on the results of pharmaceutical tests performed in the clinics located in Nagareyama (Chiba prefecture), Sendai (Miyagi prefecture), Oomiya (Saitama prefecture), and Kichijyoji (Tokyo) in Japan, and the data with regard to the diseases other than atopic dermatitis in Table 1 are based on the results of pharmaceutical tests performed in the clinic in Nagareyama.

It should be noted that no side effects were observed in the 300 cases described above. Furthermore, the external therapeutic compositions for dermatitis according to the present invention exhibit therapeutical effects in the treatment of dermatitis diseases which have been very difficult to be cured such as atopic dermatitis or seborrhea dermatitis. In addition, 99% of the effective rate can be obtained in the treatment of seborrhea dermatitis or acne.

The external therapeutic compositions for dermatitis according to the present invention can exhibit 90% or more of the effective rate with regard to all diseases shown in Table 1. Some patients did not need the external therapeutic compositions of the present invention in approximately 7 days~30 days. In addition, by applying an aqueous solution containing polysaccharides other than adrenal cortical steroid dissolved in water (Japanese Patent No. 1,597,430) to the affected part, the disease was completely cured.

FORMULATION EXAMPLE 2

| | |
|---|---|
| Dextran | 10 g |
| Glucose | 5 g |
| Maltose | 10 g |
| Mannitol | 5 g |
| Sodium chloride | 0.1 g |
| Potassium chloride | 0.2 g |
| Sodium betamethasone phosphate | 0.06 g |
| Cyclodextrin | 10 g |
| Purified water | 59.58 g |
| Total | 100.0 g |

FORMULATION EXAMPLE 3

| | |
|---|---|
| Pullulan | 10 g |
| Betain | 15 g |
| Maltose | 10 g |
| Sodium chloride | 0.1 g |
| Dexamethasone | 0.06 g |
| Cyclodextrin | 15 g |
| Purified water | 49.84 g |
| Total | 100.0 g |

FORMULATION EXAMPLE 4

| | |
|---|---|
| Dextran | 5 g |
| Betain | 20 g |
| Maltose | 5 g |
| Sodium chloride | 0.1 g |
| Sodium dexamethasone phosphate | 0.05 g |
| Cyclodextrin | 15 g |
| Purified water | 54.85 g |
| Total | 100.0 g |

FORMULATION EXAMPLE 5

| | |
|---|---|
| Dextran | 10 g |
| Hydroxyethyl cellulose | 2 g |
| Betain | 10 g |
| Mannitol | 10 g |
| Calcium chloride | 0.1 g |
| Sodium chloride | 0.1 g |
| Dextrin | 7 g |
| Sodium dexamethasone phosphate | 0.1 g |
| Cyclodextrin | 10 g |
| Purified water | 50.7 g |
| Total | 100.0 g |

FORMULATION EXAMPLE 6

| | |
|---|---|
| Pullulan | 15 g |
| Hydroxyethyl cellulose | 10 g |
| Betain | 15 g |
| Mannitol | 5 g |
| Calcium chloride | 0.1 g |
| Sodium chloride | 0.1 g |
| Dextrin | 7 g |
| Dexamethasone | 0.05 g |
| Cyclodextrin | 15 g |
| Purified water | 32.75 g |
| Total | 100.0 g |

It was observed that the effects of Formulation Examples 2~6 followed the effects of Formulation Example 1. These formulations can be selected depending on the conditions of the dermatitis.

In the following, comparative formulations and the pharmaceutical effects thereof are shown.

COMPARATIVE FORMULATION EXAMPLE 1

| | |
|---|---|
| Betamethasone valerate | 0.12 g |
| Methyl paraoxybenzoate | 0.15 g |

-continued

| | |
|---|---|
| White vaseline | 99.73 g |
| Total | 100.0 g |

COMPARATIVE FORMULATION EXAMPLE 2

| | |
|---|---|
| Betamethasone valerate | 0.12 g |
| Methyl paraoxybenzoate | 0.15 g |
| Surfactant | 30 |
| White vaseline | 69.73 g |
| Total | 100.0 g |

In the following, the effects of Comparative Formulation Example 1 are shown in Table 2.

TABLE 2

| Disease | Number of Subjects | Effectiveness (Points) | Effective Rate (%) |
|---|---|---|---|
| Atopic dermatitis (1) | 10 | 2 | 10 |
| Atopic dermatitis (2) | 50 | 5 | 5 |
| Atopic dermatitis (3) | 25 | 5 | 10 |
| Atopic dermatitis (4) | 50 | 7 | 7 |
| Seborrhea dermatitis (3) | 50 | 5 | 5 |
| Eczema | 100 | 18 | 9 |

Table 2 shows the results of the pharmaceutical tests with regard to Comparative Formulation Example 1. In Table 2, "Effectiveness", "Effective rate", and clinics where the pharmaceutical tests were carried out are the same as described in Formulation Example 1.

According to the results of the pharmaceutical tests with regard to Comparative Formulation Example 1 which has an oily base, the comparative formulation did not exhibit nearly the level of curing effects as did those of the present invention, and caused adverse effects, i.e., in some cases, the condition was worsened by employing Comparative Formulation Example 1, leading to a termination of the use thereof. Furthermore, it was generally observed that the effective rate of the comparative formulation was adversely affected by the number of dosing days.

From the above observations, it can be concluded that since the comparative formulation according to Comparative Formulation Example 1 inhibits keratinization, which is a physiological function of skin, because of the oily base in the formulation, the disease cannot be improved. In some cases, the oily base actually worsens the condition.

On the other hand, in Formulation Example 1 of the external therapeutic composition according to the present invention, the aqueous base never inhibits the physiological functions of skin. Furthermore, the ingredients added in the aqueous base provide the same conditions as a cellular interstitial fluid on the cellular surface, promoting the normalization of the cells. Therefore, the composition according to the present invention may produce strong pharmaceutical effects as anti-inflammatory adrenal cortical steroid agent.

As described above, it is demonstrated that the present invention can achieve the stated objects. In other words, according to the present invention, by virtue of dissolving the therapeutically effective amount of an adrenal cortical steroid clathrated in a cyclodextrin, in an aqueous solution including polysaccharides, there are no disadvantages such that the oily ingredients employed in the conventional base dissolve the horny layer of the skin, inhibiting the regeneration of the normal skin.

In addition, by virtue of employing 0.025% by weight to 0.5% by weight of adrenal cortical steroid such as dextran, pullulan, or the like, 0.2% by weight to 30% by weight of cyclodextrin, and 0.5% by weight to 55% by weight of polysaccharides, as well as, an aqueous solution of polysaccharides including glucose, mutan, lentinan, sodium chloride, calcium chloride, and the like, the external therapeutic composition according to the present invention can prevent the intracellular-respiration inhibition caused by the disfunction of the mitochondrial membrane and lowering in production of ATP (adenosine triphosphate) which is the active source of cells. Furthermore, the external therapeutic composition according to the present invention can maintain the electrolyte balance and osmotic pressure balance, as well as produce the pharmaceutical effects of the adrenal cortical steroid.

As a result, since the aqueous base in the composition does not inhibit the physiological function of the skin, a synergistic effect between the natural healing power which the living organism has per se and the adrenal cortical steroid agent can be obtained. Therefore, the external therapeutic composition according to the present invention can produce strong therapeutical effects in the treatment of atopic dermatitis, eczema, or the like in which the conventional oily base exhibits poor therapeutical effects.

In addition, since the total amount of the adrenal cortical steroid employed up to the complete cure is reduced, the inhibition of pituitary—adrenal cortex functions, as well as the side effects such as functional disease in eyes and the other organs, caused by the use of a large amount of the adrenal cortical steroid, may not be observed.

As described above, the external therapeutic composition for dermatitis according to the present invention can produce an extremely increased effective rate, as compared with the conventional external composition for dermatitis, and can produce therapeutical effects especially in the treatment of diseases such as atopic dermatitis, seborrhea dermatitis, and the like, which have been very difficult to be cured. Therefore, since the external therapeutic composition for dermatitis according to the present invention can replace the conventional external composition for dermatitis there is great improvement in effectiveness from the viewpoints of curing rate and safety, i.e., very low levels of side effects are observed. It may be expected that the external composition according to the present invention will be administered to many patients now suffering from difficult-to-treat dermatitis.

Finally, the present application claims the priority on Japanese Patent Application No. Hei 7-346006, filed on Dec. 11, 1995, which is herein incorporated by reference.

What is claimed is:

1. An external therapeutic composition for dermatitis comprising a therapeutically effective amount of an adrenal cortical steroid, a cyclodextrin, polysaccharides, and a carriers, wherein the external therapeutic composition comprises 0.025% by weight to 0.5% by weight of adrenal cortical steroid, 0.2% by weight to 30% by weight of cyclodextrin, and 0.5% by weight to 55% by weight of polysaccharides.

2. The external therapeutic composition as recited in claim 1, wherein the adrenal cortical steroid is clathrated in the cyclodextrin.

3. The external therapeutic composition as recited in claim 1, wherein the aqueous solution contains a clathrate of adrenal cortical steroid in cyclodextrin, dissolved in an aqueous solution of polysaccharides.

4. The external therapeutic composition as recited in claim 1, wherein the polysaccharides is dextran or pullulan.

5. The external therapeutic composition as recited in claim 3, wherein the aqueous solution of polysaccharides further comprises glucose, mutan, lentinan, sodium chloride, calcium chloride, and potassium chloride.

6. A method for the treatment of dermatitis in a mammalian subject, which comprises administering to said subject a therapeutically effective amount of an external therapeutic composition for dermatitis comprising a therapeutically effective amount of an adrenal cortical steroid, a cyclodextrin, polysaccharides, and a carrier, wherein the external therapeutic composition comprises 0.025% by weight to 0.5% by weight of adrenal cortical steroid, 0.2% by weight to 30% by weight of cyclodextrin, and 0.5% by weight to 55% by weight of polysaccharides.

7. The method as recited in claim 6, wherein the adrenal cortical steroid is clathrated in the cyclodextrin.

8. The method as recited in claim 6, wherein the aqueous solution contains a clathrate of adrenal cortical steroid in cyclodextrin, dissolved in an aqueous solution of polysaccharides.

9. The method as recited in claim 6, wherein the polysaccharides is dextran or pullulan.

10. The method as recited in claim 8, wherein the aqueous solution of polysaccharides further comprises glucose, mutan, lentinan, sodium chloride, calcium chloride, and potassium chloride.

* * * * *